United States Patent

Hirota et al.

[11] Patent Number: 6,015,449
[45] Date of Patent: Jan. 18, 2000

[54] RAIN DROP DETECTING DEVICE

[75] Inventors: Koichi Hirota, Anjo; Kohki Ohara, Nishio; Kazuyoshi Mori, Chiryu, all of Japan

[73] Assignee: Aisin Seiki Kabushiki Kaisha, Kariya, Japan

[21] Appl. No.: 09/022,631

[22] Filed: Feb. 12, 1998

[51] Int. Cl.⁷ ............................... G01N 29/20; B06B 3/02
[52] U.S. Cl. .................... 75/599; 73/170.17; 318/483; 318/DIG. 2; 340/602
[58] Field of Search .................. 73/597, 599, 170.17, 73/DIG. 1; 318/443–446, 460, 483, 643, DIG. 2; 15/250.12, DIG. 15; 340/580, 582, 602, 962

[56] References Cited

U.S. PATENT DOCUMENTS

| | | | |
|---|---|---|---|
| 4,584,508 | 4/1986 | Kobayashi et al. | 318/483 |
| 4,604,612 | 8/1986 | Watkins et al. | 340/582 |
| 5,187,980 | 2/1993 | Blair et al. | 73/599 |
| 5,203,207 | 4/1993 | Sugiyama | 73/170.17 |
| 5,432,415 | 7/1995 | Ittah et al. | 318/483 |
| 5,539,289 | 7/1996 | Wiget | 318/483 |

FOREIGN PATENT DOCUMENTS

| | | |
|---|---|---|
| 2163848 | 7/1987 | Japan . |
| 4-78641 | 3/1992 | Japan . |
| 0227768 | 8/1998 | Japan . |

*Primary Examiner*—Hezron Williams
*Assistant Examiner*—Rose M. Miller
*Attorney, Agent, or Firm*—Burns, Doane, Swecker & Mathis, LLP

[57] ABSTRACT

A rain drop detecting device includes an oscillation element disposed on a plate member such as a windshield for generating an ultrasonic wave on the plate member, an ultrasonic wave receiving element disposed on the plate member for receiving the ultrasonic wave generated by the oscillation element, a detecting device connected to the ultrasonic wave receiving element for detecting an amplitude of the ultrasonic wave, and an ultrasonic wave absorbing member disposed on the plate member. The absorbing member is designed to absorb a portion of the ultrasonic wave generated by the oscillation element to prevent the downwardly travelling portion of the ultrasonic wave from travelling beyond a desired region of the plate member. In the case of a windshield, the absorbing member can be used to prevent the ultrasonic wave from travelling to the resting location of the wiper so that inadvertent rain drop detection does not occur.

17 Claims, 3 Drawing Sheets

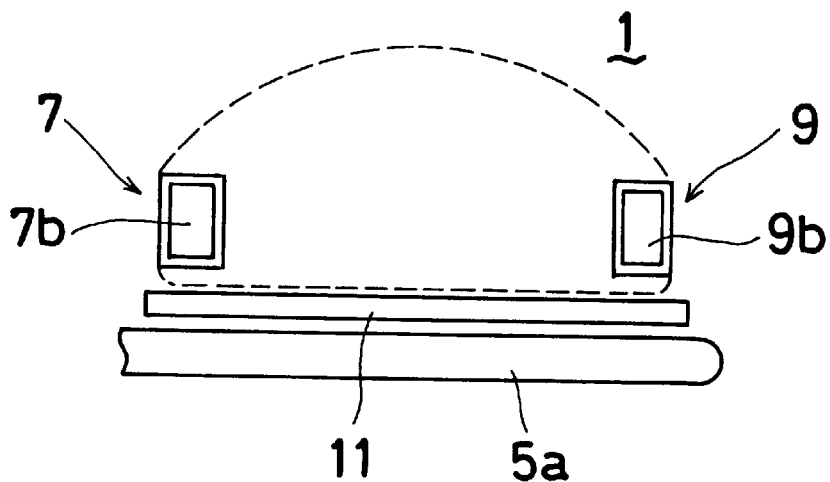
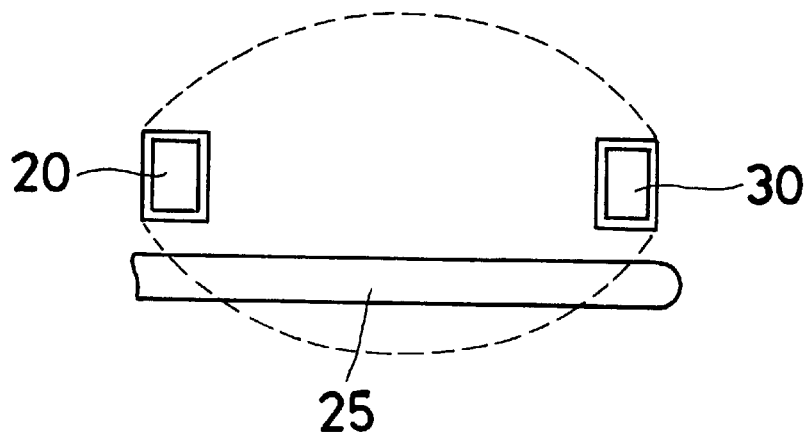

RAIN DROP DETECTING DEVICE

The present application is based on Japanese Patent Application No. 09 (1997)-29242, the entire disclosure of which is incorporated herein by reference.

FIELD OF THE INVENTION

The present invention generally relates to a rain drop detecting device. More particularly, the present invention pertains to a rain drop detecting device for detecting rain drops on a vehicle windshield.

BACKGROUND OF THE INVENTION

A conventional rain drop detecting device is disclosed in Japanese Patent Laid-Open Publication No. 4 (1992)-78641. The rain drop detecting device disclosed in this publication includes a detecting unit comprised of a wave sending element and a wave receiving element, each of which is formed with a piezoelectric vibrator. The detecting unit is disposed at the lower portion of the front window of a vehicle. In this way, the driver's view is not obstructed and the detecting device does not detract from the vehicle's attractive appearance.

However, in accordance with this construction, when a large amount of rain water is on the front window of the vehicle and is being wiped by the windshield wiper, the water has a tendency to stick to the wiper. Because the detecting unit is disposed at the lower portion of the front window of the vehicle, the detecting unit has a tendency to detect the water on the wiper, even though the windshield may be clear of water. The detecting unit thus inadvertently detects a large quantity of rain drops on the windshield and so the wiper blade is frequently operated even though rain water on the windshield has been wiped away.

FIG. 4 illustrates the reason for the aforementioned problem. As illustrated in FIG. 4, the detecting device includes vibrators 20, 30, and the area of the windshield over which the ultrasonic wave is generated is represented by the region enclosed within the pair of arched broken lines. As can be seen, the ultrasonic wave is transmitted towards both the upper and lower portions of the windshield because there is no structure that obstructs the transmission of the ultrasonic wave. Thus, the detecting area covers not only the upper region of the windshield, but also the lower region of the windshield where the wiper 25 is positioned during non-operation. This then causes the detecting device to inadvertently detect water on the wiper 25 which is in the stored position. Consequently, water drops are detected even in situations where the windshield is already clear of water drops.

In light of the foregoing, a need exists for a rain drop detecting device that is able to precisely detect the amount of rain drops falling on a vehicle windshield.

It would be desirable to also provide a rain drop detecting device that is low in cost, relatively simple in structure and small in size.

SUMMARY OF THE PRESENT INVENTION

To address the foregoing needs, the present invention provides a vehicle windshield rain drop detecting device that includes an oscillation element disposed on the vehicle windshield for generating an ultrasonic wave on the windshield, an ultrasonic wave receiving element disposed on the windshield in spaced apart relation to the oscillation element for receiving the ultrasonic wave generated by the oscillation element, a detecting device connected to the ultrasonic wave receiving element for detecting an amplitude of the ultrasonic wave received by the ultrasonic wave receiving element, and an absorbing member disposed on the windshield for absorbing a portion of the ultrasonic wave generated by the oscillation element. The absorbing member is disposed on the windshield between the oscillation element and the location of the windshield wiper during non-operation.

Another aspect of the invention involves a vehicle windshield rain drop detecting device that includes an oscillation element disposed on the vehicle windshield for generating an ultrasonic wave on the windshield, an ultrasonic wave receiving element disposed on the windshield for receiving the ultrasonic wave generated by the oscillation element, a detecting device connected to the ultrasonic wave receiving element for detecting an amplitude of the ultrasonic wave received by the ultrasonic wave receiving element, and a device positioned between the oscillation element and the lower edge of the windshield for preventing a portion of the ultrasonic wave travelling towards the lower edge of the windshield from travelling beyond the device.

According to a further aspect of the invention, a rain drop detecting device for detecting rain drops includes an oscillation element disposed on a plate member for generating an ultrasonic wave on the plate member, an ultrasonic wave receiving element disposed on the plate member for receiving the ultrasonic wave generated by the oscillation element, a detecting device connected to the ultrasonic wave receiving element for detecting an amplitude of the ultrasonic wave received by the ultrasonic wave receiving element, and an absorbing member disposed on the plate member for absorbing a portion of the ultrasonic wave generated by the oscillation element.

BRIEF DESCRIPTION OF THE DRAWING FIGURES

The foregoing and additional features associated with the present invention will become more readily apparent from the following detailed description considered with reference to the accompanying drawing figures in which like elements are designated by like reference numerals and wherein:

FIG. 3 is a top view of the rain drop detecting device of the present invention; and FIG. 4 is a top view of the rain drop detecting device of the prior art.

DETAILED DESCRIPTION OF THE INVENTION

Figure 1:
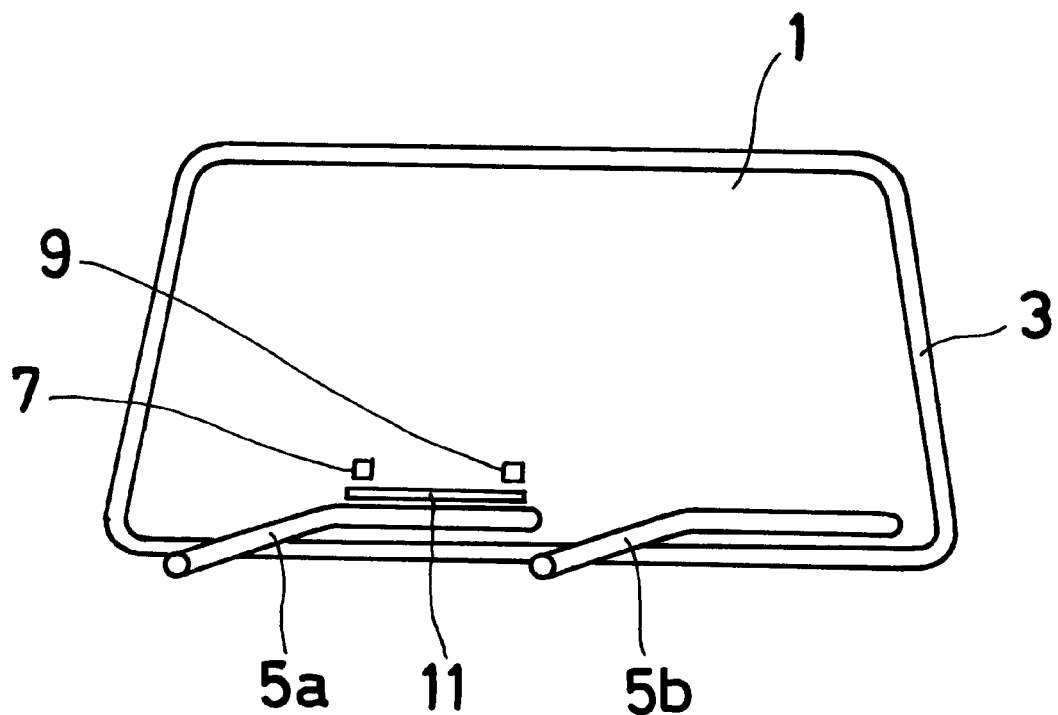
FIG. 1 is a front view of the front window or windshield of a vehicle on which is disposed the rain drop detecting device of the present invention.

With reference initially to FIG. 1, the rain drop detecting device of the present invention is installed on the front window glass or front windshield 1 of a vehicle. The windshield 1 is mounted on the vehicle body through a window molding 3. A pair of wipers 5a, 5b are installed on the vehicle body and are located at the lower portion of the windshield 1. The wipers 5a, 5b are adapted to swing back and forth during operation for purposes of wiping the windshield 1 and clearing away water drops. A detailed discussion of the features and operation of the wipers 5a, 5b is not included here as such features and manner of operation are conventional and known to those skilled in the art.

An oscillating wave generating element 7 for generating or sending an ultrasonic wave and an ultrasonic wave receiving element 9 for receiving the ultrasonic wave generated by the oscillating wave generating element 7 are adhered to the reverse surface of the windshield 1. That is, the oscillating wave generating element 7 and the ultrasonic wave receiving element 9 are adhered to the interior surface of the windshield 1 that faces towards and is exposed to the inside of the vehicle compartment. The oscillating wave generating element 7 and the ultrasonic wave receiving element 9 are mounted on the windshield 1 in a spaced apart manner from one another so as to be separated from each other by a distance. Both the oscillating wave generating element 7 and the ultrasonic wave receiving element 9 can be formed of, for example, a piezoelectric vibrator. The oscillating element 7 generates an ultrasonic wave across the windshield 1.

An ultrasonic wave absorbing member 11 for absorbing a portion of the ultrasonic wave is also adhered to the reverse surface or inside surface of the windshield 1. The absorbing member 11 is designed to absorb the downwardly travelling portion of the ultrasonic wave which would otherwise extend downwardly to the wiper 5a. The absorbing member 11 prevents the portion of the ultrasonic wave travelling downwardly towards the lower edge of the windshield 1 from travelling beyond the absorbing member 11.

The absorbing member 11 can be adhered in place on the windshield in a variety of ways such as through the use of glue, a double coated sensitive adhesive tape, or the like. As illustrated in FIG. 1, the absorbing member 11 is positioned between one of the wipers 5a and each of the oscillating wave generating element 7 and the ultrasonic wave receiving element 9. Thus, the oscillating wave generating element 7 and the ultrasonic wave receiving element 9 are located vertically above the absorbing member 11 on the surface of the windshield 1. The entirety of the absorbing element 11 is spaced from the lower edge of the windshield 1 and is spaced from the window molding 3 as seen in FIG. 1 The absorbing member 11 can be formed of, for example, an adhesive tape made of a non-foaming type acrylic resin, although other materials possessing the desired characteristics could also be used.

Figure 2:
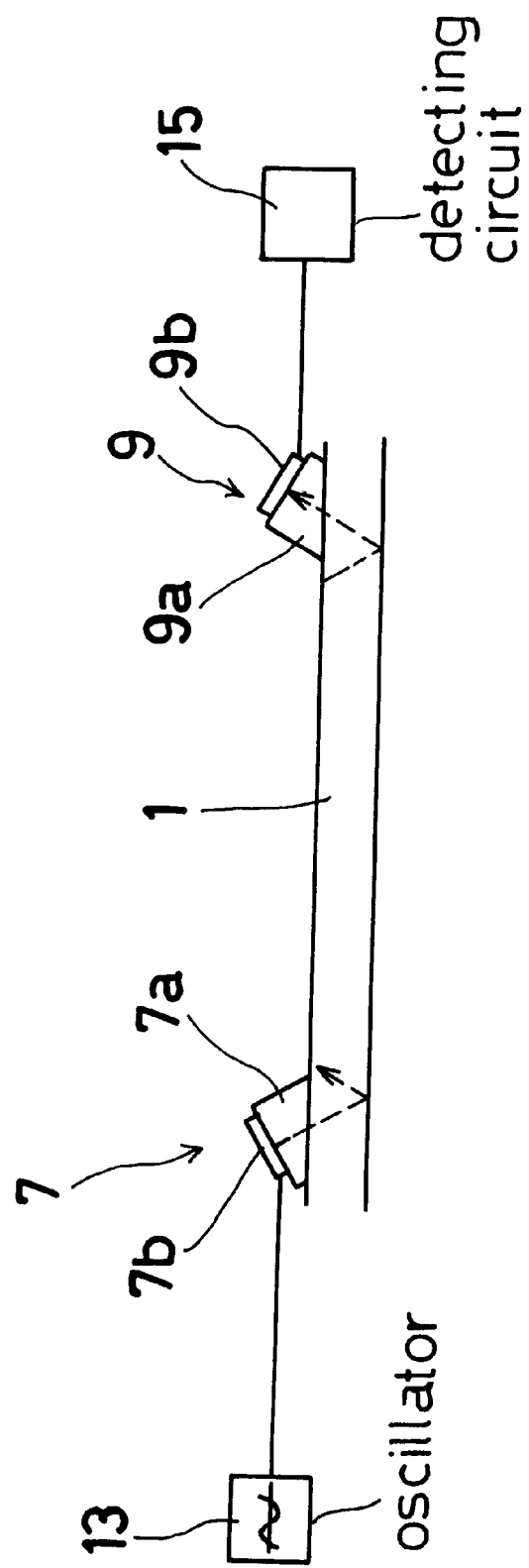
FIG. 2 is a side view of the rain drop detecting device of the present invention.

As shown in FIG. 2, the oscillating element 7 includes a coupler 7a which is disposed on the windshield 1 and a piezoelectric vibrator 7b which is adhered to the coupler 7a. The ultrasonic wave receiving element 9 includes a coupler 9a which is disposed on the windshield 1 and a piezoelectric vibrator 9b which is adhered to the coupler 9a.

The piezoelectric vibrator 7b is connected to an oscillator 13 which supplies an alternating current. The piezoelectric vibrator 7b oscillates primarily in the thickness direction thereof due to the alternating current supplied by the oscillator 13. The piezoelectric vibrator 7b thus generates an ultrasonic wave on the windshield 1 through the coupler 7a. The transmitted or generated ultrasonic wave is schematically illustrated in FIG. 2 by the dashed line and arrow.

The ultrasonic wave generated or transmitted on the windshield 1 oscillates the piezoelectric vibrator 9b mainly in the thickness direction thereof through the coupler 9a. A detecting circuit 15 which is connected to the piezoelectric vibrator 9b detects the amount of alternating current (or voltage) in order to sense the amplitude of the oscillation of the piezoelectric vibrator 9b.

The ultrasonic wave which is generated by the oscillating wave generating element 7 is transmitted upward towards the upper portion of the windshield 1 over a wide area indicated by the arched broken line in FIG. 3. This is possible because there exists no structure to prevent the ultrasonic wave from being transmitted to the upper portion of the windshield 1.

On the other hand, the transmission of the ultrasonic wave towards the lower portion of the windshield 1 is limited by the absorbing member 11. That is, the ultrasonic wave is unable to cross or extend beyond the absorbing member 11 as shown in FIG. 3 because the absorbing member 11 absorbs the ultrasonic wave.

The area of the windshield 1 over which the ultrasonic wave is transmitted, which area is generally designated by the dotted line area in FIG. 3, constitutes the detecting area of the rain drop detecting device of the present invention. When rain drops fall in this area of the windshield 1 generally indicated by the broken line outline depicted in FIG. 3, the amplitude of the oscillation of the piezoelectric vibrator 9b is varied by the diffused reflection of the ultrasonic wave approaching the rain drops on the windshield 1. The detecting circuit 15 detects this variation in the amplitude of the oscillation of the piezoelectric vibrator 9b and is thus able to detect that rain drops exist on the windshield 1. The wipers 5a, 5b are thus operated to clear away water drops on the windshield 1.

As shown in FIG. 3, the portion of the windshield 1 which is located near the wiper 5a is out of the detecting area of the rain drop detecting device of the present invention because of the presence of the absorbing member 11 which obstructs the transmission of the ultrasonic wave to the lower portion of the windshield 1. As noted above, the absorbing member 11 is positioned such that the oscillating wave generating element 7 and the ultrasonic wave receiving element 9 are positioned on one side of the absorbing member 11, while the wipers in the rest or non-operational state are positioned on the opposite side of the absorbing member 11. Ultrasonic waves which are generated and transmitted across the windshield 1 are thus prevented from travelling to the portion of the windshield at which the wipers are located in the rest or non-operational state. Consequently, although rain water drops may stick to or be present on the wiper 5a, the rain drop detecting device does not detect such rain water and thus does not inadvertently and incorrectly determine that there are rain drops on the windshield.

By virtue of the present invention, the rain drop detecting device is able to accurately and reliably detect the presence of rain drops on the windshield, without inadvertently sensing the presence of rain drops on the wipers. This is accomplished in a relatively inexpensive and simple manner, thus not requiring significant expenditure for implementation.

The principles, preferred embodiment and mode of operation of the present invention have been described in the foregoing specification. However, the invention which is intended to be protected is not to be construed as limited to the particular embodiment described. Further, the embodiment described herein is to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the invention be embraced thereby.

What is claimed is:

1. A rain drop detecting device for detecting rain drops on a vehicle windshield, comprising:

an oscillation element disposed on a vehicle windshield for generating an ultrasonic wave on the windshield, the windshield having associated therewith a wiper which during non-operation is at a first location and which during operation moves across at least a portion of the windshield to remove rain drops;

an ultrasonic wave receiving element for receiving the ultrasonic wave generated by the oscillation element, the ultrasonic wave receiving element being disposed on the windshield in spaced apart relation to said oscillation element:

detecting means connected to the ultrasonic wave receiving element for detecting an amplitude of the ultrasonic wave received by the ultrasonic wave receiving element, with the amplitude of the ultrasonic wave received by the ultrasonic wave receiving element indicating a presence or absence of rain drops on the windshield; and an absorbing member for absorbing a portion of the ultrasonic wave which is generated by the oscillation element, the absorbing member being disposed on the windshield between the oscillation element and said first location.

2. A rain drop detecting device as recited in claim 1, wherein the absorbing member is made of a non-foaming acrylic resin.

3. A rain drop detecting device as recited in claim 1, wherein the oscillation element includes a coupler mounted on the windshield and a piezoelectric vibrator which is secured to the coupler.

4. A rain drop detecting device as recited in claim 1, wherein the ultrasonic wave receiving element includes a coupler which is mounted on the windshield and a piezoelectric vibrator which is secured to the coupler.

5. A rain drop detecting device for detecting rain drops on a vehicle windshield, comprising:

an oscillation element disposed on a vehicle windshield for generating an ultrasonic wave on the windshield, the windshield having a lower edge;

an ultrasonic wave receiving element for receiving the ultrasonic wave generated by the oscillation element, the ultrasonic wave receiving element being disposed on the windshield:

a detecting device connected to the ultrasonic wave receiving element for detecting an amplitude of the ultrasonic wave received by the ultrasonic wave receiving element, with a variation in the amplitude of the ultrasonic wave received by the ultrasonic wave receiving element indicating a presence of rain drops on the windshield; and means positioned between the oscillation element and the lower edge of the windshield for preventing a portion of the ultrasonic wave travelling towards the lower edge of the windshield from travelling beyond said preventing means.

6. A rain drop detecting device as recited in claim 5, wherein said preventing means is made of a non-foaming acrylic resin.

7. A rain drop detecting device as recited in claim 5, wherein said preventing means is an ultrasonic wave absorbing element.

8. A rain drop detecting device as recited in claim 5, wherein the oscillation element includes a coupler mounted on the windshield and a piezoelectric vibrator which is secured to the coupler.

9. A rain drop detecting device as recited in claim 5, wherein the ultrasonic wave receiving element includes a coupler which is mounted on the windshield and a piezoelectric vibrator which is secured to the coupler.

10. A rain drop detecting device as recited in claim 5, wherein the windshield has an outer periphery, and including a molding extending around the outer periphery of the windshield.

11. A rain drop detecting device for detecting rain drops, comprising:

an oscillation element disposed on a plate member for generating an ultrasonic wave on the plate member;

an ultrasonic wave receiving element for receiving the ultrasonic wave generated by the oscillation element, the ultrasonic wave receiving element being disposed on the plate member:

detecting means connected to the ultrasonic wave receiving element for detecting an amplitude of the ultrasonic wave received by the ultrasonic wave receiving element, with the amplitude of the ultrasonic wave received by the ultrasonic wave receiving element indicating a presence or absence of rain drops on the plate member; and an absorbing member for absorbing a portion of the ultrasonic wave generated by the oscillation element, the absorbing member being disposed on the plate member and to one side of the oscillation element and the ultrasonic wave receiving element.

12. A rain drop detecting device as recited in claim 11, wherein the absorbing member is made of a non-foaming acrylic resin.

13. A rain drop detecting device as recited in claim 11, wherein the oscillation element includes a coupler mounted on the plate member and a piezoelectric vibrator which is secured to the coupler.

14. A rain drop detecting device as recited in claim 11, wherein the ultrasonic wave receiving element includes a coupler which is mounted on the plate member and a piezoelectric vibrator which is secured to the coupler.

15. A rain drop detecting device as recited in claim 11, wherein the plate member is a vehicle windshield.

16. A rain drop detecting device as recited in claim 15, wherein the absorbing member is disposed between a wiper arm and both the oscillation element and the ultrasonic wave receiving element.

17. A rain drop detecting device as recited in claim 11, wherein the plate member includes a lower edge, said absorbing member being spaced from the lower edge of the plate member.

* * * * *

UNITED STATES PATENT AND TRADEMARK OFFICE
CERTIFICATE OF CORRECTION

PATENT NO. : 6,015,449
DATED : January 18, 2000
INVENTOR(S) : K. HIROTA, et al.

It is certified that error appears in the above-identified patent and that said Letters Patent is hereby corrected as shown below:

On the Title Page:
The following information is added:

[30]         Foreign Application Priority Data

Feb. 13, 1997     [JP]     Japan ...................... 9-29242

Signed and Sealed this

Twenty-seventh Day of March, 2001

Attest:

NICHOLAS P. GODICI

Attesting Officer      Acting Director of the United States Patent and Trademark Office